US006835176B2

United States Patent
McNair

(10) Patent No.: US 6,835,176 B2
(45) Date of Patent: Dec. 28, 2004

(54) COMPUTERIZED SYSTEM AND METHOD FOR PREDICTING MORTALITY RISK USING A LYAPUNOV STABILITY CLASSIFIER

(75) Inventor: Douglas S. McNair, Leawood, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

(21) Appl. No.: 10/751,821

(22) Filed: Jan. 5, 2004

(65) Prior Publication Data
US 2004/0225201 A1 Nov. 11, 2004

Related U.S. Application Data

(60) Provisional application No. 60/468,765, filed on May 8, 2003.

(51) Int. Cl.[7] .................................................. A61B 5/00
(52) U.S. Cl. ........................................ 600/300; 128/920
(58) Field of Search ................................. 600/300–301, 600/508, 509, 515; 128/920, 925, 923–924; 706/924; 702/19; 607/5

(56) References Cited

U.S. PATENT DOCUMENTS 5,201,321 A * 4/1993 Fulton ........................ 600/515
6,438,419 B1 * 8/2002 Callaway et al. ........... 600/508

* cited by examiner

Primary Examiner—Max F. Hindenburg
Assistant Examiner—Michael Astorino
(74) Attorney, Agent, or Firm—Shook, Hardy & Bacon L.L.P.

(57) ABSTRACT

A method and system suitable for automated surveillance of intensive care unit patients for information denoting likelihood of in-hospital survival or mortality, represented in the timeseries of scoring systems such as APACHE III. Techniques from digital signal processing and Lyapunov stability analysis are combined in a method that allows for optimization of statistical hypothesis testing that is robust against short time series of as few as five time points. Once optimized, the method and system can achieve high-sensitivity high-specificity classification of survivorship, while avoiding false-positive prediction of morality.

1 Claim, 3 Drawing Sheets

*Processing Steps for Determining Stability by Lyapunov Exponent*

*Processing Steps for Determining Stability by Lyapunov Exponent*

Lyapunov Exponents for Survivors, vs. Time (days).

Lyapunov Exponents for Nonsurvivors, vs. Time (days).

COMPUTERIZED SYSTEM AND METHOD FOR PREDICTING MORTALITY RISK USING A LYAPUNOV STABILITY CLASSIFIER

CROSS-REFERENCE TO RELATED APPLICATIONS

This application claims the benefit of U.S. Provisional Application No. 60/468,765 filed May 8, 2003.

STATEMENT REGARDING FEDERALLY SPONSORED RESEARCH OR DEVELOPMENT

Not applicable.

TECHNICAL FIELD

The present invention relates to a system and method for identifying which individual persons admitted to an intensive care unit (ICU) are likely to die prior to hospital discharge, and which persons are likely to recover and survive to discharge.

BACKGROUND OF THE INVENTION

A very difficult clinical problem facing clinicians is knowing when further treatment is futile and no longer appropriate in a patient who has developed severe complications after surgery and is being treated in an ICU. It is now possible to prolong the process of dying among such patients. This results in unnecessary pain and loss of dignity for the patient, anguish and distress for the patient's relatives and is dehumanizing for the clinical and nursing staff. It has also tremendous implications in the use of limited health care resources.

The complementary clinical problem facing clinicians, that of knowing when further aggressive treatment is appropriate and has reasonable odds of saving the patient's life and yielding quality of life and other benefits in addition to survival, is equally difficult. Prognostic criteria based on "static" analysis of group statistics are of little value in decisions to withhold or withdraw therapy from ICU patients too ill to benefit, since they do not provide adequate information on the features that distinguish non-survivors from survivors.

In 1990, Smedira and co-workers (Smedira 1990) wrote that "life support is withheld or withdrawn from many patients especially those with critical illness, but the exact number is not known." The terms 'withholding of life support' and 'withdrawal of life support' refer to the process according to which various medical interventions either are withheld from patients or discontinued with the expectation that the patient will die as a result.

The feeling that a patient admitted to the ICU should not be considered as a 'terminal patient' produces difficulties associated with rationalizing the use of new and costly technologies in a situation where resources are scarce, such as the modern healthcare systems. This has led to the development of new systems for the assessment of severity for use in the ICU. These tools may be used to predict outcome, although their use has ethical and financial implications.

Over the last 15 years, several systems for the assessment of multiorgan failure have been developed, mainly because multiorgan failure represents the main cause of mortality and morbidity among critically ill patients managed in the ICU.

A computer model designed to improve the process of decision-making concerning the continuation or escalation of aggressive ICU interventions, or of abating interventions that are probably futile, must possess the following properties: it must reflect the time-dependent, or "dynamic", pathophysiological process and be able to predict death with high accuracy, early in the clinical course when there is but a scanty timeseries comprised of very few (<10) values of predictive scores or physiologic indices of end-organ function. It is important to emphasize that serial scoring is not purely a reflection of the inherent potential of the patient's organ systems to recover function sufficient to sustain life; it reflects the ability of an intensive care unit to stabilize the patient or reverse the physiological dysfunction that is present.

Prior art includes Chang's algorithm (Chang 1988), which used computerized dynamic trend analysis of daily organ failure scores (APACHE II score, corrected for the number and duration of organ failures), noting the rate of change in score relative to that of the previous day and an absolute threshold to predict death. The algorithm was developed by tracking the daily scores of 200 ICU patients until their death or discharge from the ICU. It was subsequently validated on 831 patients. Chang's approach had poor sensitivity (predicted only 38% of all deaths) with acceptable statistical specificity (no false-positive predictions). More recent trend analysis techniques such as SOFA ('sequential organ failure assessment', see Cook 2001, Hutchinson 2000, Pettila 2002, Rosenberg 2002) continue to suffer from inadequate sensitivity.

Other algorithms using serial scoring have had unacceptably high false-positive rates. For example, Atkinson's study (Atkinson 1994) showed a false-positive diagnosis rate of 4.4%. If used prospectively, this algorithm does have the potential to indicate the futility of continued intensive care but at the high cost of nearly 1 in 20 patients who would survive if intensive care were continued.

Chang's and others' approaches were unsatisfactory in terms of excessive reliance on long timeseries (74% of predictions resolvable by trend analysis required data from seven days or more in the ICU, too long to be of significant help in the contemporary situation with its focus on prompt decision-making soon after admission and aggressive discharge-planning). In part, the failure of the prior art can be traced to inappropriate pooling of data from groups of patients with markedly differing mortality rates, including many whose probability of in-hospital death was low or moderate. For this reason and many others, there is a need for a system and method overcoming the deficiencies of the prior art.

REFERENCES

Atkinson S, et al. Identification of futility in intensive care. *Lancet*. 1994 Oct. 29;344(8931):1203–6.

Chang R W, et al. Predicting outcome among intensive care unit patients using computerised trend analysis of daily Apache II scores corrected for organ system failure. *Intensive Care Med*. 1988;14:558–66.

Chang R W, Bihari D S. Outcome prediction for the individual patient in the ICU. *Unfallchirurg*. 1994 April;97 (4): 199–204.

Christakis N A, Asch D A. Biases in how physicians choose to withdraw life support. *Lancet*. 1993;342:642–6.

Cook R, et al. Multiple organ dysfunction: baseline and serial component scores. *Crit Care Med*. 2001 November;29(11):2046–50.

De Queiroz M S, et al. Lyapunov-Based Control of Mechanical Systems. Birkhauser, 2000.

Elger C E. Nonlinear EEG analysis and its potential role in epileptology. *Epilepsia*. 2000;41 Suppl 3:S34–8.

Freeman R A, Kokotovic P V. Robust Nonlinear Control Design: State-Space and Lyapunov Techniques. Springer Verlag, 1996.

Goldberger A L, West B J. Applications of nonlinear dynamics to clinical cardiology. *Ann New York Acad. Sci.* 1987;504: 155–212.

Goldberger A L. Non-linear dynamics for clinicians: chaos theory, fractals, and complexity at the bedside. *Lancet.* 1996; 347:1312–4.

Hutchinson C, et al. Sequential organ scoring as a measure of effectiveness of critical care. *Anesthesia.* 2000 December;55(12):1149–54.

Knaus W A, Wagner D P. Multiple systems organ failure: epidemiology and prognosis. *Crit Care Clin.* 1989 April;5 (2):221–32.

Lakshmikantham V, et al. Vector Lyapunov Functions and Stability Analysis of Nonlinear Systems. Kluwer, 1991.

Pai M A. Power System Stability: Analysis by the Direct Method of Lyapunov. Elsevier, 1981.

Pettila V, et al. Comparison of multiple organ dysfunction scores in the prediction of hospital mortality in the critically ill. *Crit Care Med.* 2002 August;30(8):1705–11.

Pool R. Is it healthy to be chaotic? *Science.* 1989;243:604–7.

Rosenberg A L. Recent innovations in intensive care unit risk-prediction models. *Curr Opin Crit Care.* 2002 August;8(4):321–30.

Smedira N G, et al. Withholding and withdrawal of life support from the critically ill. *N Engl J. Med.* 1990;322:309–15.

Wagner D P, et al. Daily prognostic estimates for critically ill adults in intensive care units: results from a prospective, multicenter, inception cohort analysis. *Crit Care Med.* 1994 September;22(9): 1359–72.

Wihstutz L, Arnold L. Lyapunov Exponents. Springer Verlag, 1986.

SUMMARY OF THE INVENTION

The present invention is a method and system mitigating the limitations enumerated above and suitable for an improved system and method for predicting mortality risk using a Lyapunov stability classifier.

In one embodiment of the present invention, a method in a computing environment for effecting a statistical assessment of mortality-predictive patterns in longitudinal timeseries data from individual persons admitted to hospital-based intensive care is provided. The method includes the following steps: accessing mortality-predictive serial data received from a plurality of scores; performing spectral analysis; calculating the Lyapunov exponent, and if the Lyapunov exponent is negative, outputting values for the exponent for a plurality of times in the timeseries.

Additional advantages and novel features of the invention will be set forth in part in a description which follows, and in part will become apparent to those skilled in the art upon examination of the following, or may be learned by practice of the invention.

BRIEF DESCRIPTION OF THE DRAWINGS

The present invention is described in detail below with reference to the attached drawing figures, wherein.

DETAILED DESCRIPTION OF THE INVENTION

Figure 1:
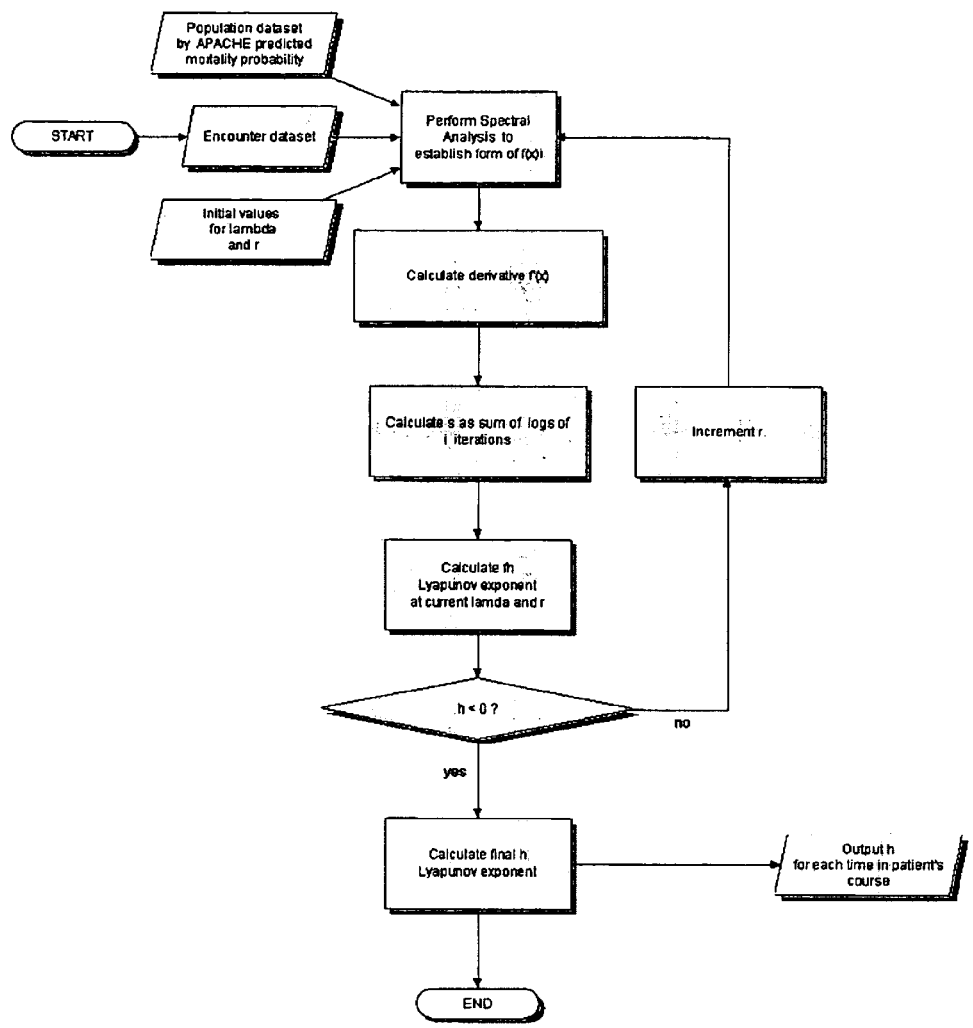
FIG. 1 is a flow chart representative of a method for predicting mortality risk in accordance with an embodiment of the present inventions, namely a method using spectral analysis and MAPLE-based determination of Lyapunov exponents.
Figure 2:
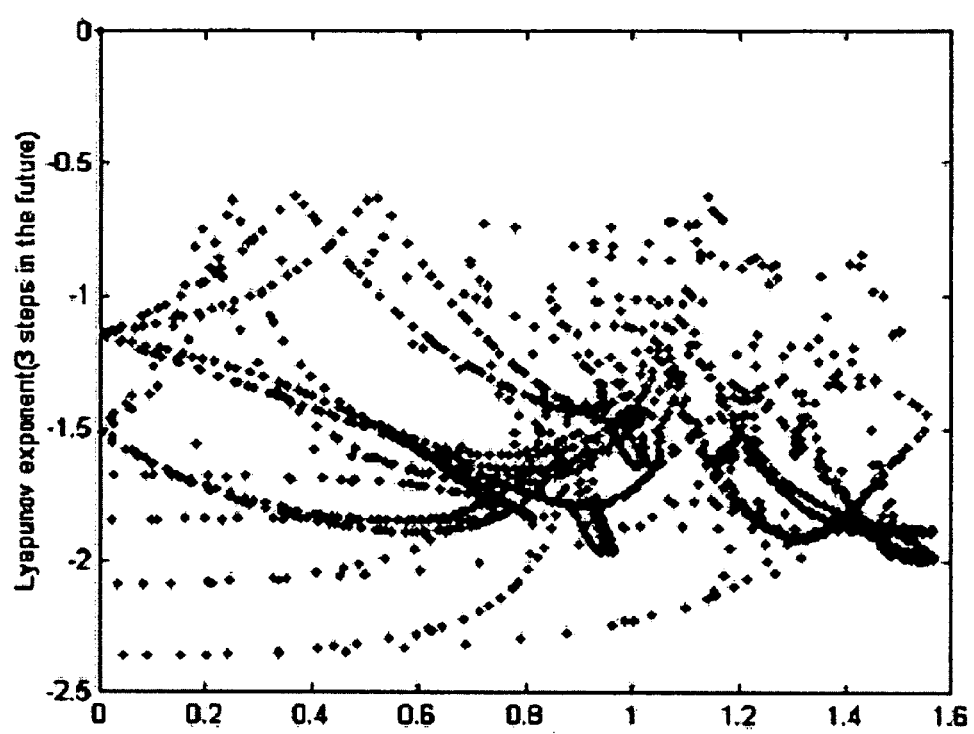
FIG. 2 is a diagram of Lyapunov exponents of non-survivors in the development dataset, for serial APACHE score timeseries as a function of time in days following admission to ICU.
Figure 3:
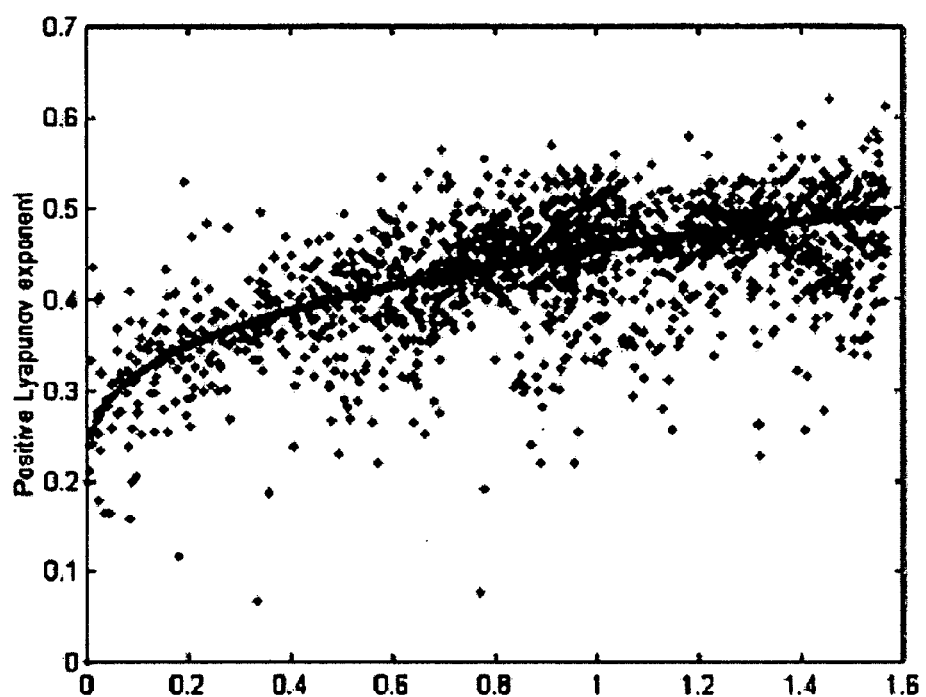
FIG. 3 is a diagram of Lyapunov exponents of survivors in the development dataset, for serial APACHE score timeseries as a function of time in days following admission to ICU.

The present invention is a method and system mitigating the limitations enumerated above and suitable for an improved system and method for predicting mortality risk using a Lyapunov stability classifier. The method and system are preferably implemented in one of a variety of known general purpose or special purpose computing system environments or configurations. Those of ordinary skill in the art will appreciate that any of a variety of components and interconnection are well known, and details concerning the construction need not be disclosed in connection with the present invention.

When "multiple organ systems failure" (MOSF) is defined as severe physiologic abnormalities, it is found to arise in the context of a wide variety of diseases. The distinguishing feature of MOSF appears not to be the underlying etiology, but the uniform and frequently fatal outcome once it develops. This indicates that MOSF may represent a final common pathway to death rather than a clinical syndrome with a single underlying etiology. Regardless of cause, evaluating the incremental impact of new therapy on MOSF will be assisted by the adoption of uniform definitions as well as by the explicit measurement of severity of disease and calculation of individual probabilities of death. And, regardless of cause, the fact that the pattern of physiologic derangements are hallmarks of the final common pathway of MOSF enables application of a unified approach to timeseries analysis.

The present invention resulted from a study of the incidence of withholding or withdrawing therapeutic measures in intensive care unit (ICU) patients, as well as the possible implications of organ failure assessment (APACHE III and SOFA) in the decision-making process and the ethical conflicts emerging from these measures.

The patients (n=372) were assigned to different groups: those surviving one year after ICU admission (S; n=301), deaths at home (DH; n=2), deaths in the hospital after ICU discharge (DIH; n=13) and deaths in the ICU (DI; n=56). The last group was divided into the following subgroups: two cardiovascular deaths (CVD), 20 brain deaths (BD), 25 deaths after withholding of life support (DWH) and nine deaths after withdrawal of life support (DWD).

APACHE III, daily therapeutic intervention scoring system (TISS) and daily SOFA scores were good mortality predictors. The length of ICU stay in DIH (20 days) and in DWH (14 days) was significantly greater than in BD (5 days) or in S (7 days). The number of days with a maximum SOFA score was greater in DWD (5 days) than in S, BD or DWH (2 days).

Daily APACHE scoring is useful when the decision to withhold or withdraw treatment has to be considered, especially if the established measures do not improve the clinical condition of the patient. Although making decisions based on the use of severity parameters may cause ethical problems, it may reduce the anxiety level. Additionally, it may help when considering the need for extraordinary measures or new investigative protocols for better management of resources.

The present invention accomplishes the following objectives:

1. To determine the incidence of withholding and withdrawing care in critically ill patients in a multidisciplinary adult ICU.
2. To evaluate whether decisions made about withholding or withdrawal of treatment and applying a pre-established protocol could be supported by the information obtained from the monitoring of indicators of severity, in other words sepsis-related organ failure assessment SOFA, TISS, and APACHE III.

3. To decrease the level of anxiety among family members and the medical team responsible for the patient's care, at the time when the decision is taken to withhold or to withdraw therapeutic management.

Prior to developing the method disclosed herein, deaths among patients admitted to the ICU were defined in relation to the type of management before death.

The patients were placed in groups according to the final outcome: those surviving one year after ICU admission (S); death at home after hospital discharge (DH); death in the hospital once discharged from the ICU (DIH); and death in the ICU (DI).

In the DI group, the cases were classified into the following subgroups according to the type of management decision taken at the time of death 1. Cardiovascular death (CVD): those patients who died despite cardiopulmonary resuscitation (CPR) for at least 30 minutes, according to hospital guidelines. This group represents a substantial investment in therapeutic resources at the time of death.

2. Brain death (BD): those patients where an irreversible loss of cerebral and brainstem function were found, following the guidelines of the American Society of Anesthesiologists and U.S. law. Once BD was confirmed, mechanical ventilation was withdrawn or was continued until organ donation was authorized.

3. Death after withholding of life support (DWH; patients in whom it was decided to limit therapy): the most common therapies withheld are CPR in the event of cardiac arrest and dialysis. Less frequently withheld therapeutic measures include mechanical ventilation, laboratory analysis, surgical procedures, administration of antibiotics, parenteral nutrition, blood transfusions, fluid therapy, antiarrhythmic drugs or vasopressors. In the ICU, the withholding of any therapeutic measure besides CPR and dialysis is rare, because either these cases would not be considered to be candidates for admission into the ICU, or the withdrawal of therapeutic measures of life support would be considered.

4. Death after the withdrawal of therapeutic life-support measures (DWD; patients in whom a gradual withdrawal of therapeutic resources of life support was carried out, after the previous establishment of withholding measures): initially, nutrition, vasopressor agents and dialysis were withdrawn. Finally, oxygen support was withdrawn and, if necessary, the respiratory frequency and the tidal volume were reduced. The patient was never disconnected from mechanical ventilation, nor was sedation stopped in any case.

The ICU doctor responsible for the patient's care, on their own initiative or after considering a proposal from the patient's family or the head of the department, proposed the need to establish therapeutic restrictions or to withdraw treatment. This opinion was discussed with the other doctors of the service and the nursing staff responsible for the patient. If the proposal was accepted, the relevant doctors from other departments who had sought the patient's admission to the ICU were asked for their opinion and, once a consensus was reached, this was conveyed to the family by the ICU doctor directly responsible for the patient.

If at any time the decision was not accepted, the required life-support measures were continued. The ICU doctor on call always respected the decisions reached. Only in rare circumstances did the on-call doctor, in agreement with the admitting doctor, decide, with the family, to withhold treatment before group discussion.

Once the patient was discharged to a general ward, the ICU doctor informed the ward doctor about the decisions taken, such as not to return to the ICU in case of deterioration in the patient's clinical condition or not to perform CPR.

Resource utilization was evaluated by measuring the use of mechanical ventilation and the daily TISS in the ICU. The daily APACHE III and the daily SOFA were used as indicators of severity. APACHE and SOFA scores were calculated for each organ system.

All patients with an ICU stay longer than 24 hours were included.

The groups were compared using the Kruskal-Wallis test and the Mann-Whitney rank-sum test, with the Tukey-B test and the Scheffe test correction for between-groups analysis. The qualitative variables were analyzed with the Chi-square test. Differences were considered significant at $P<0.05$. Groups with small samples ($<5$) were excluded from the statistical analyses. All statistical analyses were performed on a personal computer with SAS Version 8 and MAPLE Version 8.

A total of 623 patients were admitted to the ICU during the study period from January 2000 through April 2002. Two hundred and fifty-one patients did not fulfill the inclusion criteria and were excluded.

A total of 372 patients were included: 68% were male, mean age ($\pm$SD) was 59$\pm$17 years (range 14–92), mean average stay in ICU was 8$\pm$10 days (range 1–81) and the 1-year mortality rate was 59% (71 cases). The mortality rate was also closely related to the need for mechanical ventilation. Of 203 cases (55%) who required mechanical ventilation, 106 died (52%).

In patients who died, APACHE III (BD: 91$\pm$31, range 34–129; DWH: 84$\pm$3, range 31–153; DWD: 81$\pm$25, range 41–113; DIH: 91$\pm$31, range 44–137) and SOFA score on the first day (BD: 9$\pm$3, range 2–16; DWH: 9$\pm$4, range 1–17; DWD: 9$\pm$4, range 1–16; DIH: 10$\pm$4, range 3–16) were significantly higher than in the S group (APACHE III: 38$\pm$24, range 2–117; SOFA score on the first day: 4$\pm$4, range 0–14; $P<0.0001$). The CVD group (APACHE III: 41$\pm$19, range 27–54; SOFA score on the first day: 2$\pm$3, range 0–4) had similar results to the S group.

The TISS score on the first day is significantly higher in the BD (34$\pm$10, range 15–53), DWH (34$\pm$11, range 16–57) and DIH groups (34$\pm$5, range 25–41) than in the S group (22$\pm$13, range 4–54; $P<0.0001$). There were no significant differences between the S group and the DWD (24$\pm$13, range 8–46) and CVD groups (15$\pm$1, range 14–16).

The mean SOFA of the S group (3$\pm$3, range 0–12) and the CVD group (4$\pm$5, range 0–7) was significantly lower than in the other groups (BD: 11$\pm$3, range 5–19; DWH: 12$\pm$4, range 4–18; DWD: 11$\pm$4, range 7–19; DIH: 8$\pm$3, range 3–11; $P<0.0001$).

Similarly the mean TISS of the S group (21$\pm$11, range 14–47) and the CVD group (21+14, range 11–31) was significantly lower than in the other groups (BD: 35$\pm$9, range 22–60; DWH: 37$\pm$11, range 15–59; DWD: 33$\pm$7, range 19–44; DIH: 31$\pm$5, range 25–41; $P<0.0001$).

ICU stay (days) was significantly shorter in the S (7$\pm$8, range 1–58), CVD (4$\pm$3, range 2–6) and BD groups (5+6, range 1–20), compared with the DWH (14+16, range 1–81) and DIH groups (20$\pm$14, range 5–44; $P<0.0001$). There were no significant statistical differences between the S and DWD groups (12$\pm$10, range 3–29).

BD (30%) and DWD (15%) were differentiated from one another, given that the medical care and ethical implications are very different in these two groups. The DWH group represented 35% of cases. While brain death caused only occasional diagnostic difficulties, the greatest ethical conflicts among the medical team responsible for the patient were caused when deciding in which patients and at what moment should therapeutic restrictions or withdrawal of life-supporting measures be suggested and established. In our study, these ethical discussions arose in 48% of patients who died.

At this point, it would be easy to generalize decision making according to these markers, as they seem to be good indicators of bad prognosis. However, decisions should be individualized for each patient, as the concepts of quality of life and dignity in death, new technologies, greater demand for health or the maintenance of sustainable or equitable medicine greatly influence the decision-making process.

With a follow-up based on objective and quantifiable data, the doctor is better informed and more accurate decisions are achieved. This is fundamental when the changes in the role of the doctor in the decision-making process are considered. The principles of autonomy and self-determination, and the new concepts of quality of life, lead to consensual medical treatment and to adequate informed written consents.

However, an APACHE score alone, or even trend analysis of serial APACHE scores, does not provide sufficient complementary information about the possible need to withdraw treatment, in particular when referring to the withdrawal of life support. Beginning a treatment is easy, but stopping it is much more difficult. The only analyzed data which may be of interest in this sense are the number of shifts with a high or increasing score. This has high sensitivity as a sign of diagnostic or treatment failure if accompanied by a Lyapunov exponent indicating instability.

In this sense, although it may be very difficult to accept a feeling of failure, the data afforded by Lyapunov assessment of serial scores may be very useful. The underlying study suggested that a patient suffering from the failure of six organs together with unfavorable APACHE scores inexorably evolved to death. These data were reinforced when the increase in the patient's APACHE score was accompanied by an equally significant increase in the TISS. The worsening of the clinical situation was maintained despite the additional therapeutic resources used.

Undoubtedly, the withdrawal of life support reduces both ICU stay and the investment of therapeutic resources (lower accumulated TISS), which has corresponding economic repercussions. However, this reduction was not statistically significant among the patients in the DWH and DIH groups.

Analysis of the data showed that patients in the DWD group were in fact subject to therapeutic restrictions from the moment of admission. This can be explained by the fact that, with similar levels of severity (APACHE III and SOFA score on the first day of ICU stay), the TISS score on the first day was lower than in the other groups of deaths. Despite this, the mean TISS was very similar. It was surprising to note that, during ICU stay, an increase of resources used was observed for the DWD group which, in the end, reached the mean for the other groups of deaths.

Another noteworthy finding was the length of time that elapsed from the beginning of therapeutic restrictions until the decision to withhold life support. It was shown that patients in whom life-support measures were withheld had previously passed an average of four days with constantly high score levels. This may be seen as a worryingly long period when costs and the optimal use of scarce resources are considered. It should also not be forgotten that, during this period, the patient is dying. It is not easy to define the 'best moment' to withdraw life-support measures without overextending an 'agonizing state' that leads to discomfort for the patient or the family. The withdrawal of all life-support measures except for mechanical ventilation may mean that the patient is maintained in a terminal situation for some time. If this situation is maintained for a few minutes or even hours, it may facilitate contact between the patient and the family during the last moments, but if prolonged for more than a night or for days, it generates significant anxiety among both the family and the team caring for the patient (Christakis 1993). The present invention enables this difficult decision-making to be approached with objectivity and greater confidence than has heretofore been practical with prior art scoring systems and trend analysis.

Lyapunov stability analysis is well known in applications involving nonlinear control systems, including military defense systems and nuclear reactor control systems (De Queiroz 2000, Freeman 1996, Lakshmikantham 1991, Pai 1981, Wihstutz 1986), but it has not previously achieved practical application in analysis of medical variables or clinical decision-support. Exploratory consideration has appeared, as related to Electroneurodiagnostic (EEG) analysis (Elger 2000) and electrocardiography (EKG) analysis (Goldberger 1996). The Lyapunov exponent is a quantitative measure of separation the trajectories that diverge widely from their initial positions. The magnitude of the Lyapunov exponent is related to how chaotic a system is. The larger the exponent, the more chaotic the system. For periodic signals, the Lyapunov exponent is zero. A random but stable signal will also have an exponent very close to zero.

Spectral analysis alone cannot distinguish a chaotic process either, but some investigators have suggested that a particular spectral pattern (one in which the power density is inversely related to frequency) is highly suggestive of a nonlinear or chaotic process (Goldberger & West 1987, Goldberger 1996). However, the diagnostic value of this 1/f pattern has also been questioned (Pool 1989).

Referring to FIG. 1, a flow diagram is provided which illustrates an embodiment of a system and method for generating the Lyapunov exponent classifier and verifying and validating whether such a detector achieves statistical sensitivity and specificity in the intended mortality range of deployment, sufficient for satisfactory performance in the use for classifying patients according to in-hospital mortality outcome.

In a preferred embodiment, a system and method of the invention includes the following steps:

Let $L(x_1, x_2, \ldots, x_n)$ be a scalar function of n components of x. $L(x)$ is positive-definite in a neighborhood N of the origin if $L(x)>0$ for all $x \neq 0$ in N and $L(0)=0$.

Let $x^*(t)=0$, $t \geq t_0$ be the zero solution of the homogeneous system $x\dot{\ }=Ax$ where $x(0)=x_0=0$. Then $x^*(t)$ is globally stable for $t \geq t_0$ if there exists $L(x)$ with the following properties in some neighborhood N of 0:

(i) $L(x)$ and its partial derivatives are continuous.
(ii) $L(x)$ is positive-definite, or $L(x)>0$.
(iii) $dL(x)/dt$ is negative-definite, or $dL(x)/dt<0$.

By (ii) the quadratic form $L(x)$ exhibits an ellipsoid curve. By (iii), the ellipsoid curve shrinks to zero. Choose $\epsilon>0$ such that $N\epsilon \subset N$ above. Any half-path starting in $N\epsilon$ remains in it because $L(x)$ is a quadratic form (by (ii)) which exhibits an ellipsoid curve that is continuous as well as its partial derivatives (by (i)). The same holds for every sufficiently small $\epsilon>0$ and hence for every sufficiently small neighborhood of the origin. The zero solution is therefore globally stable. This is the case for APACHE III score timeseries of 99% of patients who are survivors to discharge from the hospital. Lyapunov exponents H for patients who did not survive were uniformly negative at some point during the ICU stay, and serve as a leading indicator of downward physiologic spiral toward death.

In other words, the system $(dx/dt)=Ax$ is globally stable if and only if for some positive-definite matrix W, the equation:

$$A'H + HA = -W$$

has a positive-definite matrix H.

If for some positive-definite matrix W, the equation $A'H+HA=-W$ has a positive-definite matrix H, let us show that (dx/dt)=Ax is globally stable. Since H is positive-definite, then $L(x)=x^t Hx$ is positive-definite (where $x^t$ is now the transpose of x and not the time derivative), i.e. $L(x)>0$. Also, $L(x)$ positive-definite implies that $V(x)$ and its partial derivatives are continuous. Differentiating $L(x)$, then:

$$dL(x)/dt=(dx^t/dt)Hx+x^t H(dx/dt)$$

or, as dx/dt=Ax:

$$dL(x)/dt=(Ax)^t Hx+x^t HAx$$

$$=x^t A^t Hx+x^t HAx$$

$$=x^t(A^t H+HA)x$$

thus, as $A^t H+HA=-W$:

$$dL(x)/dt=x^t(-W)x$$

W determined to be positive-definite implies that −W is negative-definite, thus:

$$dL(x)/dt=x^t(-W)x<0$$

Finally, it is notable that (i) $L(x)$ and its partial derivatives are continuous; (ii) $V(x)$ is positive-definite; (iii) $dL(x)/dt$ is negative-definite. As a result, dx/dt is globally stable according to our previous theorem. Conversely, if dx/dt=Ax is stable, then for some positive-definite matrix W, the equation $A^t H+HA=-W$ has a positive-definite matrix H. dx/dt=Ax stable implies all the eigenvalues of A are negative, i.e. $\lambda<0$ for any eigenvalue $\lambda$ of A. Now, as $\lambda x=Ax$, then $(Ax)^t=(\lambda x)^t$, which implies $x^t A^t=\lambda x^t$. Thus, premultiplying $A^t H+AH$ by $x^t$ and postmultiplying it by x, the following is obtained:

$$x^t(A^t H+HA)x=x^t(-W)x$$

or:

$$x^t A^t Hx+x^t HAx=x^t(-W)x$$

or substituting in $\lambda x^t$ and $\lambda x$:

$$\lambda x^t Hx+x^t H\lambda x=x^t(-W)x$$

or simply:

$$2\lambda x^t Hx=x^t(-W)x$$

As −W is negative-definite, then $x^t(-W)x<0$, thus $2\lambda x^t Hx<0$. As $\lambda<0$ by the assumption of stability, then it must be that $x^t Hx>0$, or H is a positive-definite matrix.

Thus, we have proven that a real n×n matrix A is a stable matrix if and only if there exists a symmetric positive-definite matrix H such that $A^t H+HA$ is negative-definite. In practice, a choice of W=I may be made and H can be solved and solve for H in the equation $A^t H+HA=-1$. The solution has the form $H=\alpha(A^t)^{-1}A^{-1}+\beta I$ where $\alpha$ and $\beta$ are constants. Thus, choosing a Lyapunov function, $L(x)=x^t Hx$, this solution is used to determine H.

A preferred embodiment of the present invention utilizes a source code implemented in the commercially available mathematics software package MAPLE. Practical implementation as part of an integrated ICU information system entails passing parameters and timeseries information to the Lyapunov program, which is executed by a server running MAPLE in client-server or batch mode.

A preferred embodiment of the present invention is attached as source code to provide an exemplary means of implementing the present invention. In the preferred embodiment, the second-order polynomial function $f(x)=r^*x^*(1-x)$ is utilized to represent the system whose stability is characterized by the present invention. Depending on the system, the system may be characterized by a function of different order or form. If the structure of a particular system is not known, the structure may be developed by Taylor series regression, spectral analysis or timeseries analysis techniques or other methods of modeling known to those of skill in the art.

Although the invention has been described with reference to the preferred embodiment illustrated in the attached drawing figures, it is noted that substitutions may be made and equivalents employed herein without departing from the scope of the invention as recited in the claims. For example, additional steps may be added and steps omitted without departing from the scope of this invention. Also, it will be understood by those skilled in the art that other scores such as the Simplified Acute Physiology Score (SAPS), SAPS II, or MPS may be used without departing from the scope of the invention.

---

```
>restart;
Calculate the Lyapunov exponent for f(x) = r*x*(1-x)
Use r = 3.80, 3.81, 3.82, 3.83, 3.84, 3.85, 3.86, 3.87, 3.88, 3.89.
Use the initial condition for intial APACHE III probability of mortality
(example 50%) x0 := 0.5.
The variable
    s = s(x0,i) := ln(|df(xi)|) + s(i−1) as the sum of the logarithms of
    the first i iterates.
We take s(x0,0) = 0, so when we take x0 = 0.5 we do not calculate the
derivative at 0.5.
The variable
    h = h(x0,i) := s(x0,i)/(i+1)
is the estimate of the Lyapunov exponent starting with the initial
condition x0 after i iterates.
(In the text, we write the dependence of s and h on the initial condition x0
and the iterate i,
but in the calculation we only use the variables s and h.)
For the first n1=20000 iterates the calculation for h(x0,i) is not
printed out.
For the next n2 =20 iterates the calculation for h(x0,i) is printed out,
which is the estimate for the
Lyapunov exponent.
f    The function f(x) = r*x*(1-x)
df   The derivative df(x) = f(x)
r:   Parameter value.
n1   The number of iterates for which the estimate of h(x0)
     is not displayed
n2   The number of iterates for which the estimate of h(x0)
     is displayed
x0:  The initial condition
>r := 3.81;
f := x -> r*x*(1-x);
df := x -> r - 2*r*x;
n1 := 20000;
n2 := 100;
>x0 := 0.5:
x := x0;
s := 0:
for i from 1 to n1 do
    x := f(x);
    s := s + ln(abs(df(x))):
od:
printf('\n\t r = %1.4f \n\n', r);
printf('\t x0 = %1.4f \n\n', x0);
printf('\t i \t\t h(x0,i) \n');
for j from 1 to n2 do
    x := f(x);
    s := s + ln(abs(df(x))):
    h := s/(j+n1):
    printf('\t %d \t %1.4f \n', j+n1, h );
od:
>r := 3.81;
f:= x -> r*x*(1-x);
df := x -> r - 2*r*x;
n1 := 20000;
```

```
n2 := 100;
>x0 := 0.2:
x := x0:
s := 0:
for i from 1 to n1 do
    x := f(x);
    s := s + ln(abs(df(x))):
od:
printf('\n\t x0 = %1.4f \n\n', x0);
printf('\t i \t\t h(x0,i) \n');
for j from 1 to n2 do
    x := f(x);
    s := s + ln(abs(df(x))):
    h := s/(j+n1):
    printf('\t %d \t %1.4f \n', j+n1, h );
od:
>r := 3.81;
f:= x -> r*x*(1-x);
df := x -> r - 2*r*x;
n1 := 20000;
n2 := 100;
>x0 := 0.3:
x := x0:
s := 0:
for i from 1 to n1 do
    x := f(x);
    s := s + ln(abs(df(x))):
od:
printf('\n\t x0 = %1.4f \n\n', x0);
printf('\t i \t\t h(x0,i) \n');
for j from 1 to n2 do
    x := f(x);
    s := s + ln(abs(df(x))):
    h := s/(j+n1):
    printf('\t %d \t %1.4f \n', j+n1, h );
od:
>r := 3.81;
f:= x -> r*x*(1-x);
df := x -> r -2*r*x;
n1 := 20000;
```

```
n2 := 100;
>x0 := 0.49:
x := x0:
s := 0:
for i from 1 to n1 do
    x := f(x);
    s := s + ln(abs(df(x))):
od:
printf('\n\t x0 = %1.4f \n\n', x0);
printf('\t i \t\t h(x0,i) \n');
for j from 1 to n2 do
    x := f(x);
    s := s + ln(abs(df(x))):
    h := s/(j+n1):
    printf('\t %d \t %1.4f \n', j+n1, h );
od:
>
```

What the invention claimed is:

1. A method in a computing environment for effecting a statistical assessment of morality-predictive patterns in longitudinal timeseries data from individual persons admitted to hospital-based intensive care, the method comprising the steps of:

accessing mortality-predictive serial data received from a plurality of scores;

performing spectral analysis;

calculating a Lyapunov exponent, and if the Lyapunov exponent is negative, outputting values for the exponent for at least one point in time in the timeseries so that the outcome for the individual person may be predicted.

* * * * *